(12) United States Patent
Iwashita et al.

(10) Patent No.: US 9,743,018 B2
(45) Date of Patent: Aug. 22, 2017

(54) RADIATION IMAGING SYSTEM

(71) Applicant: CANON KABUSHIKI KAISHA, Tokyo (JP)

(72) Inventors: Atsushi Iwashita, Saitama-shi (JP); Toshio Kameshima, Kumagaya (JP); Tomoyuki Yagi, Honjo (JP); Katsuro Takenaka, Honjo (JP); Hideyuki Okada, Honjo (JP); Sho Sato, Saitama (JP); Eriko Sato, Tokyo (JP); Takuya Ryu, Kokubunji (JP)

(73) Assignee: Canon Kabushiki Kaisha, Tokyo (JP)

( * ) Notice: Subject to any disclaimer, the term of this patent is extended or adjusted under 35 U.S.C. 154(b) by 70 days.

(21) Appl. No.: 14/903,271

(22) PCT Filed: Jul. 7, 2014

(86) PCT No.: PCT/JP2014/068018
§ 371 (c)(1),
(2) Date: Jan. 6, 2016

(87) PCT Pub. No.: WO2015/005262
PCT Pub. Date: Jan. 15, 2015

(65) Prior Publication Data
US 2016/0134818 A1    May 12, 2016

(30) Foreign Application Priority Data
Jul. 9, 2013 (JP) .................................. 2013-143832

(51) Int. Cl.
*H04N 5/32* (2006.01)
*H04N 5/361* (2011.01)
*A61B 6/00* (2006.01)

(52) U.S. Cl.
CPC ............. *H04N 5/32* (2013.01); *A61B 6/4233* (2013.01); *A61B 6/585* (2013.01); *H04N 5/361* (2013.01)

(58) Field of Classification Search
CPC ........ A61B 6/4233; A61B 6/585; H04N 5/32; H04N 5/361
See application file for complete search history.

(56) References Cited

U.S. PATENT DOCUMENTS

2011/0235775 A1*   9/2011   Tada ..................... A61B 6/00
                                                          378/36
2012/0211666 A1*   8/2012   Amitani .................. H04N 5/32
                                                         250/394
(Continued)

FOREIGN PATENT DOCUMENTS

JP    2010-124025 A    6/2010
JP    2012-176155 A    9/2012
JP    2012-191599 A   10/2012

*Primary Examiner* — Mark R Gaworecki
(74) *Attorney, Agent, or Firm* — Canon USA Inc., IP Division

(57) ABSTRACT

A radiation imaging system capable of obtaining excellent image quality is provided. The radiation imaging system includes a detection unit (205) configured to include a plurality of pixels which are arranged in a matrix and which output pixel values by converting radial rays into charges and to output image information, driving control means (204) for causing the plurality of pixels to perform a resetting operation until a signal indicating irradiation with radial rays is supplied and to stop the resetting operation and perform an operation of accumulating charges when the signal indicating irradiation with radial rays is supplied, and for performing an operation of reading pixel values of the plurality of pixels after the irradiation with radial rays is terminated so as to output image information corresponding to the irradiation with radial rays, correction coefficient (Continued)

obtaining means (207) for calculating correction coefficients in accordance with the image information output from the detection unit, and image correction means (208) for correcting the image information output from the detection unit using the correction coefficients calculated by the correction coefficient obtaining means.

20 Claims, 12 Drawing Sheets

(56) References Cited

U.S. PATENT DOCUMENTS

| | | | | |
|---|---|---|---|---|
| 2012/0217410 A1* | 8/2012 | Amitani | ............... | H04N 5/367 |
| | | | | 250/370.09 |
| 2013/0223592 A1* | 8/2013 | Sato | ............... | A61B 6/4233 |
| | | | | 378/62 |
| 2015/0189194 A1* | 7/2015 | Tajima | ............... | A61B 6/4233 |
| | | | | 378/62 |

\* cited by examiner

101: TFT
102: CONVERSION ELEMENT
103: BIAS POWER UNIT
104: VARIABLE GAIN AMPLIFIER
105: INTEGRATION AMPLIFIER
106: AMPLIFICATION CIRCUIT
107: SAMPLE-AND-HOLD CIRCUIT
108: MULTIPLEXER
109: OUTPUT BUFFER AMPLIFIER
110: A/D CONVERTER
111: REFERENCE POWER UNIT
112: DETECTION UNIT
113: READING CIRCUIT
114: VERTICAL DRIVING CIRCUIT
115: CURRENT/VOLTAGE CONVERSION CIRCUIT

Vs(y)   :   BIAS CURRENT IN y-th ROW

R(y)    :   SUM OF GAIN COMPONENTS OF PIXEL VALUES IN y-th ROW $$R(y) = \sum_x D(x, y) - \text{offset} * X$$

$$d(y) = 1 / \left\{ \left( \frac{Vs(\text{stop}) * R(y) * (1 - \text{depth})}{R(\text{stop}) * Vs(y)} * \text{depth} \right) + 1 \right\}$$

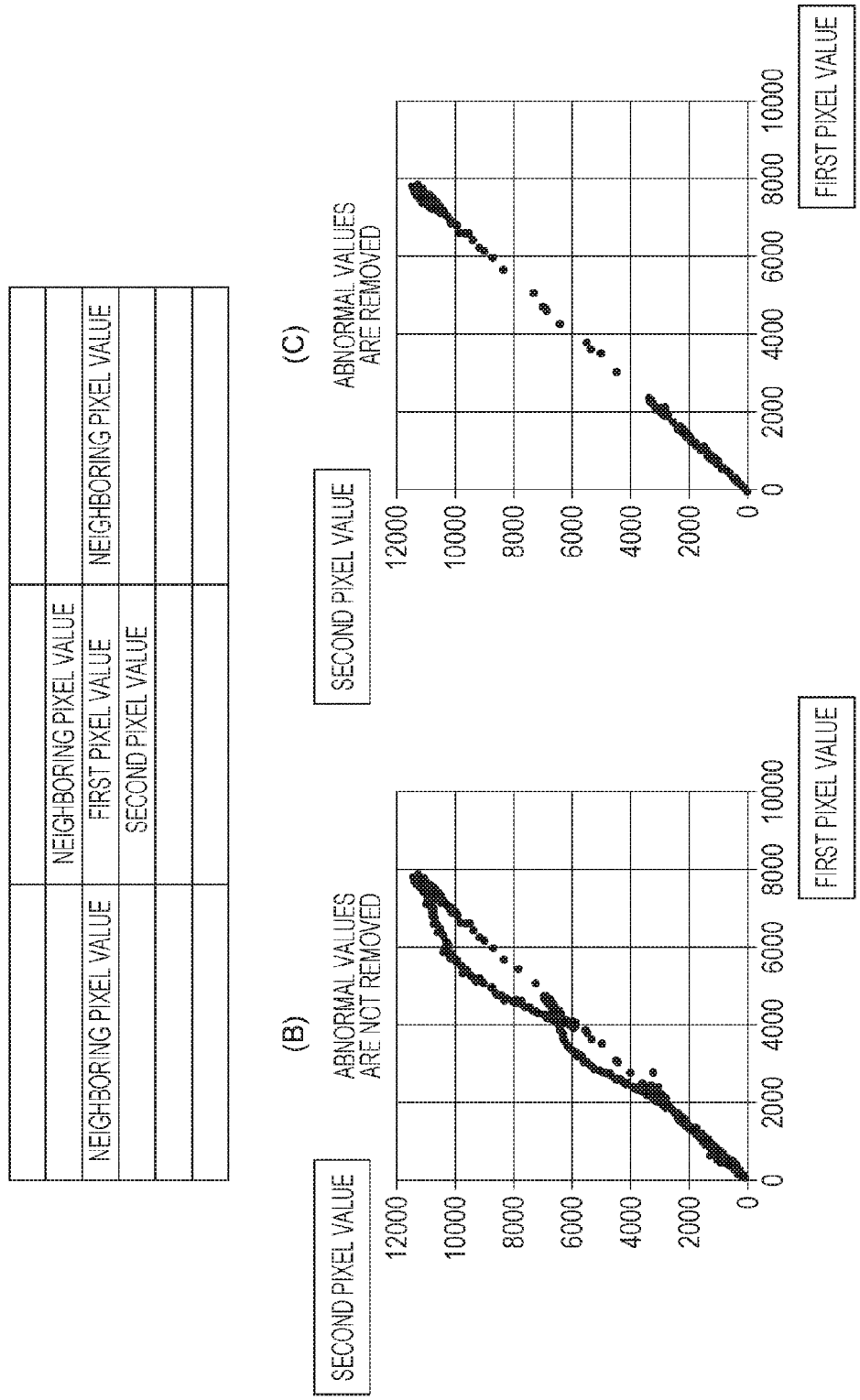

RADIATION IMAGING SYSTEM

TECHNICAL FIELD

The present invention relates to a radiation imaging system suitably used for still image shooting, such as general imaging, and moving image shooting, such as fluorography, in medical diagnosis.

BACKGROUND ART

In recent years, as an imaging apparatus used for medical image diagnosis and non-destructive inspection using X rays, a radiation imaging apparatus utilizing a flat panel detector (hereinafter referred to as an FPD) formed of a semiconductor member has been widely used. Such a radiation imaging apparatus is used as a digital imaging apparatus which performs still-image shooting, such as general shooting, and moving-image shooting, such as fluorography, in medical image diagnosis, for example. Such an imaging apparatus is generally configured such that the FPD is synchronized with an X-ray generation apparatus. However, when the FPD is installed, the FPD is required to be connected to the X-ray generation apparatus, and therefore, an installation location of the FPD is restricted.

In PTL 1, a reading circuit periodically performs a reading operation in a state in which all switch means is in an off state before imaging of a radiation image. Then a process of converting charge leaked from radiation detection elements into leakage data and a process of resetting the radiation detection elements are alternately performed in a repetitive manner using switch means so that start of irradiation with radial rays is detected in accordance with the read leakage data.

CITATION LIST

Patent Literature

PTL 1: Japanese Patent Laid-Open No. 2012-191599

SUMMARY OF INVENTION

Technical Problem

If a configuration in which an imaging operation is entered after irradiation with radial rays is detected is employed, a long period of time may be required from when the irradiation with radial rays is actually started to when start of the irradiation with radial rays is detected by a radiation imaging apparatus. Therefore, a portion of effective charge generated in pixels which have been subjected to the reading process and the resetting process may leak to signal lines, and accordingly, a line defect may occur in an image.

Accordingly, in PTL1, a range of image data including the defect is specified by analyzing a profile of image data in a direction in which the signal lines extend in the radiation imaging apparatus, and image data in the specified range is corrected. With this method, even if a line defect is unavoidably generated in an image, the line defect may be appropriately corrected and a radiation image which does not include the line defect may be reliably generated.

However, an offset component generated due to dark current or the like is added to the image data read from the radiation imaging apparatus in addition to degradation of a gain component caused by the reading process and the resetting process. If the image is corrected while the offset component is ignored, artifact is generated in the corrected image. Specifically, the correction is required to be performed after an offset correction coefficient and a gain correction coefficient are calculated. However, there arises a problem in that an offset correction coefficient and a gain correction coefficient may not be calculated from the profile of the image.

An object of the present invention is to provide a radiation imaging system capable of attaining excellent image quality by calculating correction coefficients.

Solution to Problem

A radiation imaging system of the present invention includes a detection unit configured to include a plurality of pixels which are arranged in a matrix and which output pixel values by converting radial rays into charges and to output image information, driving control means for causing the plurality of pixels to perform a resetting operation until a signal indicating irradiation with radial rays is supplied and to stop the resetting operation and perform an operation of accumulating charges when the signal indicating irradiation with radial rays is supplied, and for performing an operation of reading pixel values of the plurality of pixels after the irradiation with radial rays is terminated so as to output image information corresponding to the irradiation with radial rays, correction coefficient obtaining means for calculating correction coefficients in accordance with the image information output from the detection unit, and image correction means for correcting the image information output from the detection unit using the correction coefficients calculated by the correction coefficient obtaining means. The correction coefficient obtaining means sets a pair of a first pixel value of a pixel included in a row which has been subjected to the resetting operation after the irradiation with radial rays is started and a second pixel value of a pixel which is included in a row which has not been subjected to the resetting operation after the irradiation with radial rays is started and which is included in a column including the pixel having the first pixel value. The correction coefficients are calculated using the pair of values which belong to different columns.

Advantageous Effects of Invention

A radiation imaging system capable of obtaining excellent image quality by correcting image information using calculated correction coefficients may be provided.

BRIEF DESCRIPTION OF DRAWINGS

FIG. 13 is a diagram illustrating a method for removing an abnormal value employed in correction coefficient obtaining means.

DESCRIPTION OF EMBODIMENTS (First Embodiment)

Figure 1:
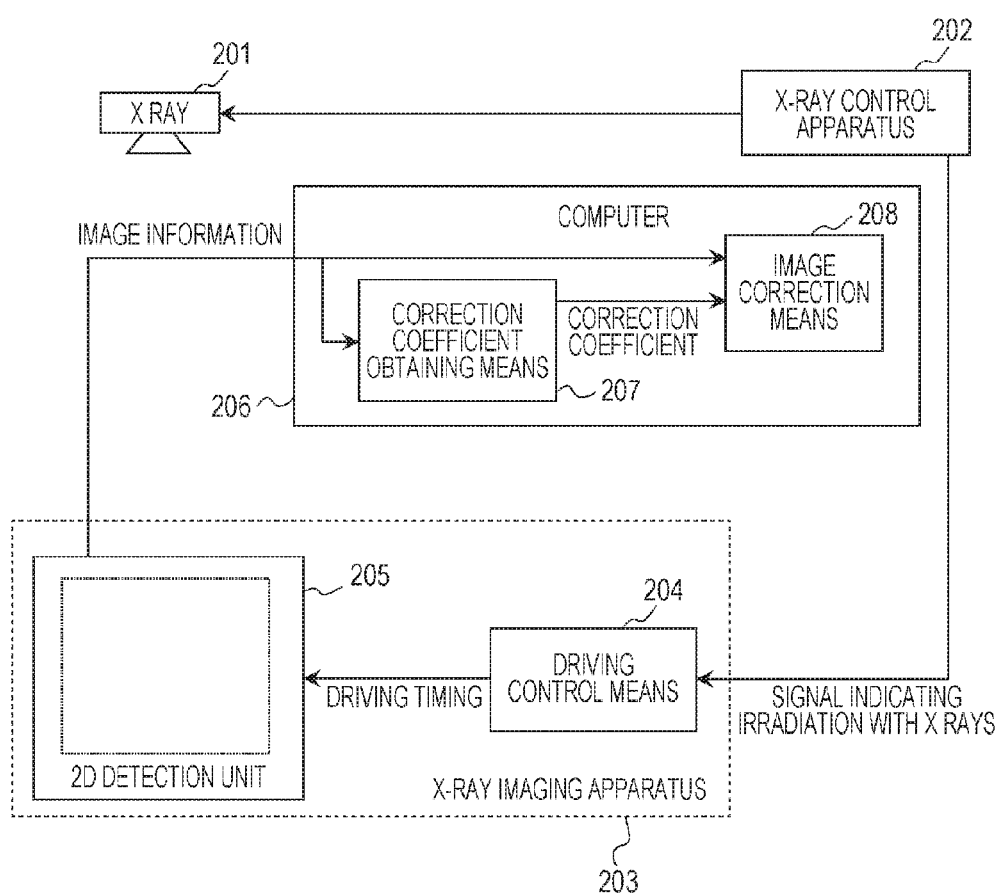
FIG. 1 is a block diagram illustrating an imaging system according to a first embodiment.

FIG. 1 is a block diagram illustrating a configuration of a radiation imaging system according to a first embodiment of the present invention. Radial rays include, in addition to beams formed of particles (including photons) emitted due to radiation disintegration, such as α-rays, β-rays, and γ-rays, X-rays, beams having energy equal to or larger than that of the beams formed of particles emitted due to radiation disintegration, such as X-rays, particle rays, and cosmic rays. Hereinafter, a case where X-rays are used as radial rays will be described. The radiation imaging system includes an X-ray generation apparatus 201, an X-ray control apparatus 202, a computer 206, and an X-ray imaging apparatus 203. The X-ray imaging apparatus 203 includes a 2D detection unit 205 and driving control means 204. The computer 206 includes correction coefficient obtaining means 207 and image correction means 208.

The X-ray control apparatus (radiation control apparatus) 202 controls irradiation with X rays of the X-ray generation apparatus 201. The X-ray generation apparatus 201 irradiates (exposes) the X-ray imaging apparatus 203 with X rays through a subject under control of the X-ray control apparatus 202. The 2D detection unit 205 is a sensor including elements which detect X rays and which are arranged in a matrix of X rows by Y columns. The 2D detection unit 205 outputs image information corresponding to the irradiation with the X rays to the computer 206 under control of the driving control means 204. A configuration of the 2D detection unit 205 will be described in detail hereinafter with reference to FIG. 2. The correction coefficient obtaining means 207 calculates correction coefficients in accordance with the image information supplied from the 2D detection unit 205 and outputs the correction coefficients to the image correction means 208. The image correction means 208 corrects the image information supplied from the 2D detection unit 205 using the correction coefficients supplied from the correction coefficient obtaining means 207. The driving control means 204 controls operation of the 2D detection unit 205 by a driving method required by the computer 206 and changes a driving method of the 2D detection unit 205 in accordance with a signal indicating the irradiation with X rays supplied from the X-ray control apparatus 202.

Figure 2:
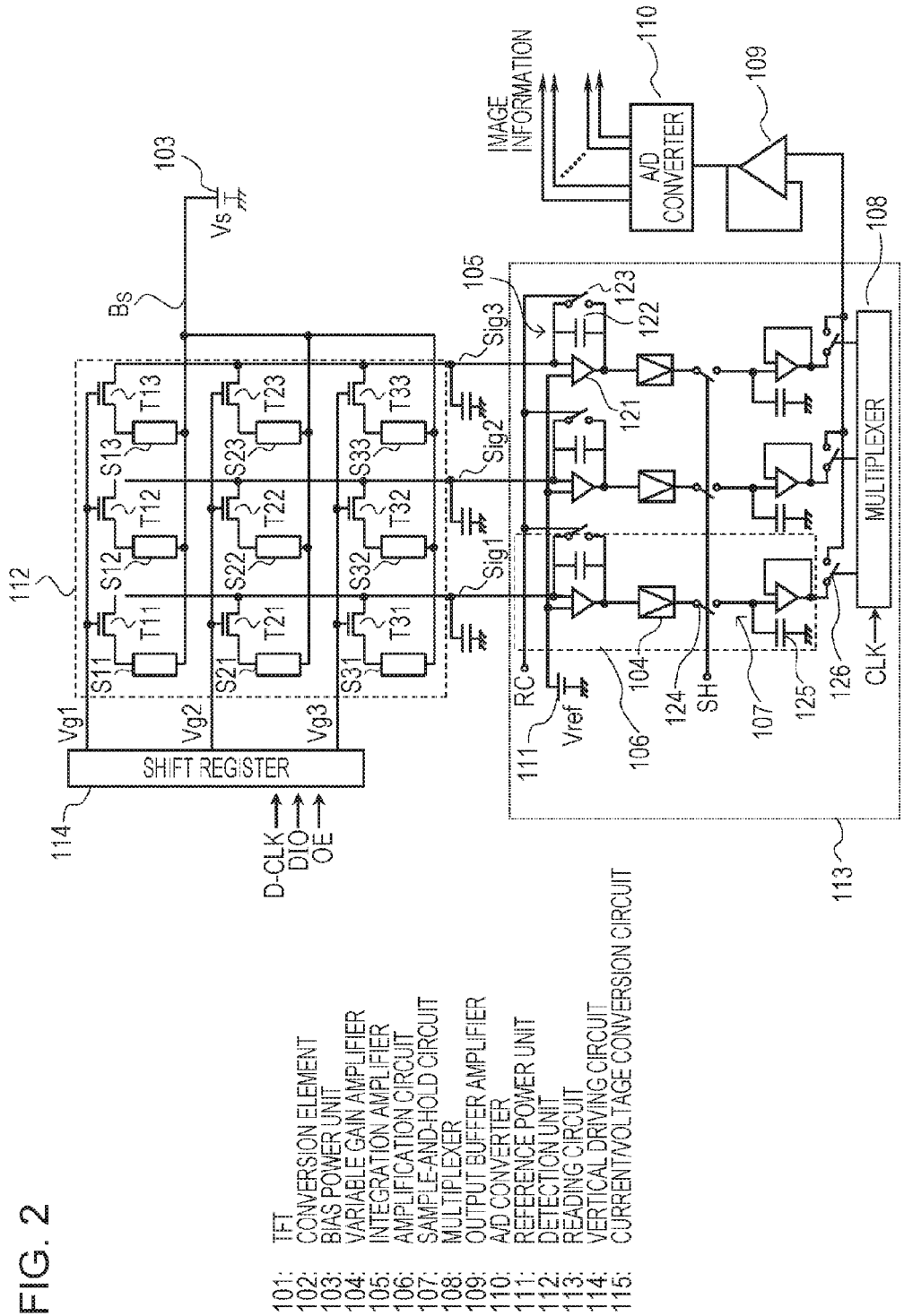
FIG. 2 is a diagram illustrating an equivalent circuit of a 2D detection unit.

FIG. 2 is a circuit diagram illustrating a configuration of the 2D detection unit 205. The 2D detection unit 205 includes a vertical driving circuit 114, a detection unit 112, a bias power unit 103, a reading circuit 113, an output buffer amplifier 109, and an analog/digital (A/D) converter 110. The 2D detection unit 205 which is a sensor including elements (pixels) which detect radial rays and which are arranged in a matrix detects radial rays and outputs image information. For simplicity of description, the detection unit 112 has pixels in a matrix of 3 rows by 3 columns, for example, in FIG. 2. However, the 2D detection unit 205 has a larger number of pixels in practice, and has pixels in a matrix of approximately 2800 rows by approximately 2800 columns in a case of 17 inches, for example.

The detection unit 112 includes a plurality of pixels arranged in a matrix. The pixels include respective conversion elements S11 to S33 which convert radial rays or light into charges and respective switch elements T11 to T33 which output electric signals corresponding to the charges of the conversion elements S11 to S33, and output pixel values. The conversion elements S11 to S33 are indirect-type conversion elements or direct-type conversion elements and convert emitted radial rays into charges. Each of the indirect conversion elements S11 to S33 includes a wavelength converter which converts a radial ray into light and a photoelectric conversion element which converts the light into charge. The direct conversion elements S11 to S33 directly convert radial rays into charges. Examples of the photoelectric conversion element which converts emitted light into charge include an MIS photodiode which is mainly formed of amorphous silicon and which is disposed on an insulating substrate, such as a glass substrate. The photoelectric conversion element may be a PIN photodiode.

Each of the switch elements T11 to T33 is a transistor having a control terminal and two main terminals and is preferably formed of a thin-film transistor (TFT). Each of the conversion elements S11 to S33 has one electrode electrically connected to one of the two main terminals of a corresponding one of the switch elements T11 to T33 and the other electrode electrically connected to the bias power unit 103 through a common bias line Bs. The bias power unit 103 supplies a bias voltage Vs to the bias line Bs. The plurality of switch elements T11 to T13 in a first row have respective control terminals which are electrically connected to a driving line Vg1 of the first row in common. The plurality of switch elements T21 to T23 in a second row have respective control terminals which are electrically connected to a driving line Vg2 of the second row in common. The plurality of switch elements T31 to T33 in a third row have respective control terminals which are electrically connected to a driving line Vg3 of the third row in common. The vertical driving circuit 114 is a shift register, for example, and controls conductive states of the switch elements T11 to T33 for individual rows by supplying a driving signal to the switch elements T11 to T33 through the driving lines Vg1 to Vg3.

Each of the plurality of switch elements T11 to T31 in a first column has ones of the main terminals connected to a corresponding one of the conversion elements S11 to S31 and the other of the main terminals electrically connected to a signal line Sig1 of the first column. While the switch elements T11 to T31 in the first column are in conductive states, electric signals corresponding to charges of the conversion elements S11 to S31 in the first column are output to the reading circuit 113 through the signal line Sig1. Each of the plurality of switch elements T12 to T32 in a second column has one of the main terminals connected to a corresponding one of the conversion elements S12 to S32 and the other of the main terminals electrically connected to a signal line Sig2 of the second column. While the switch elements T12 to T32 in the second column are in conductive states, electric signals corresponding to charges of the conversion elements S12 to S32 in the second column are output to the reading circuit 113 through the signal line Sig2. Each of the plurality of switch elements T13 to T33 in a third column has one of the main terminals connected to a corresponding one of the conversion elements S13 to S33 and the other of the main terminals electrically connected to a signal line Sig3 of the third column. While the switch elements T13 to T33 in the third column are in conductive states, electric signals corresponding to charges of the conversion elements S13 to S33 in the third column are output to the reading circuit 113 through the signal line Sig3. The plurality of signal lines Sig1 to Sig3 arranged in a column direction output electric signals supplied in parallel from the plurality of pixels to the reading circuit 113.

The reading circuit 113 includes amplification circuits 106 which amplify the electric signals supplied from the signal lines Sig1 to Sig3 in the respective signal lines Sig1 to Sig3. Each of the amplification circuits 106 includes an integration amplifier 105, a variable gain amplifier 104, and a sample-and-hold circuit 107. The integration amplifier 105 amplifies the electric signal supplied from a corresponding one of the signal lines Sig1 to Sig3. The variable gain amplifier 104 amplifies the electric signal supplied from the integration amplifier 105 by a variable gain. The sample-and-hold circuits 107 samples and holds the electric signal amplified by the variable gain amplifier 104. The integration amplifier 105 includes a calculation amplifier 121 which amplifies and outputs the electric signal supplied from a corresponding one of the signal lines Sig1 to Sig3, an integration capacitance 122, and a reset switch 123. The integration amplifier 105 may change a gain (an amplification rate) by changing a value of the integration capacitance 122. The calculation amplifier 121 in each column has an inverting input terminal connected to a corresponding one of the signal lines Sig1 to Sig3, a non-inverting input terminal connected to a reference power unit 111 having a reference voltage Vref, and an output terminal which outputs an amplified electric signal. The reference power unit 111 supplies the reference voltage Vref to the non-inverting input terminals of the individual calculation amplifiers 121. The integration capacitance 122 is disposed between the inverting input terminal and the output terminal of the calculation amplifier 121. The sample-and-hold circuit 107 includes a sampling switch 124 of a control signal SH and a sampling capacitance 125. The reading circuit 113 further includes switches 126 for the individual columns and a multiplexer 108. The multiplexer 108 successively outputs electric signals supplied in parallel from the individual amplification circuits 106 to the output buffer amplifier 109 as serial signals by successively bringing the switches 126 in the individual columns into conductive states. The output buffer amplifier 109 performs impedance conversion on the electric signals to be output. The A/D converter 110 converts the analog electric signals supplied from the output buffer amplifier 109 into digital electric signals to be output to the computer 206 illustrated in FIG. 1 as image information.

The vertical driving circuit 114 outputs driving signals having conductive voltages for bringing the switch elements T11 to T33 into conductive state and nonconductive voltages for bringing the switch elements T11 to T33 into nonconductive states to the driving lines Vg1 to Vg3 in accordance with control signals D-CLK, OE, and DIO supplied from the driving control means 204 illustrated in FIG. 1. In this way, the vertical driving circuit 114 controls the conductive states and the nonconductive states of the switch elements T11 to T33 and drives the detection unit 112. The control signal D-CLK is a shift clock of the shift register used as the vertical driving circuit 114. The control signal DIO is a transfer pulse of the shift register of the vertical driving circuit 114. The control signal OE is an output enabling signal of the shift register of the vertical driving circuit 114.

In this way, the vertical driving circuit 114 sets a driving time and a scanning direction. Furthermore, the driving means 204 outputs a control signal RC, the control signal SH, and a control signal CLK to the reading circuit 113 so as to control operations of the components included in the reading circuit 113. The control signal RC is supplied to control operation of the reset switch 123 in the integration amplifier 105. The control signal SH is supplied to control the sampling switch 124 in the sample-and-hold circuit 107. The control signal CLK is a clock signal supplied to control operation of the multiplexer 108.

Figure 3:
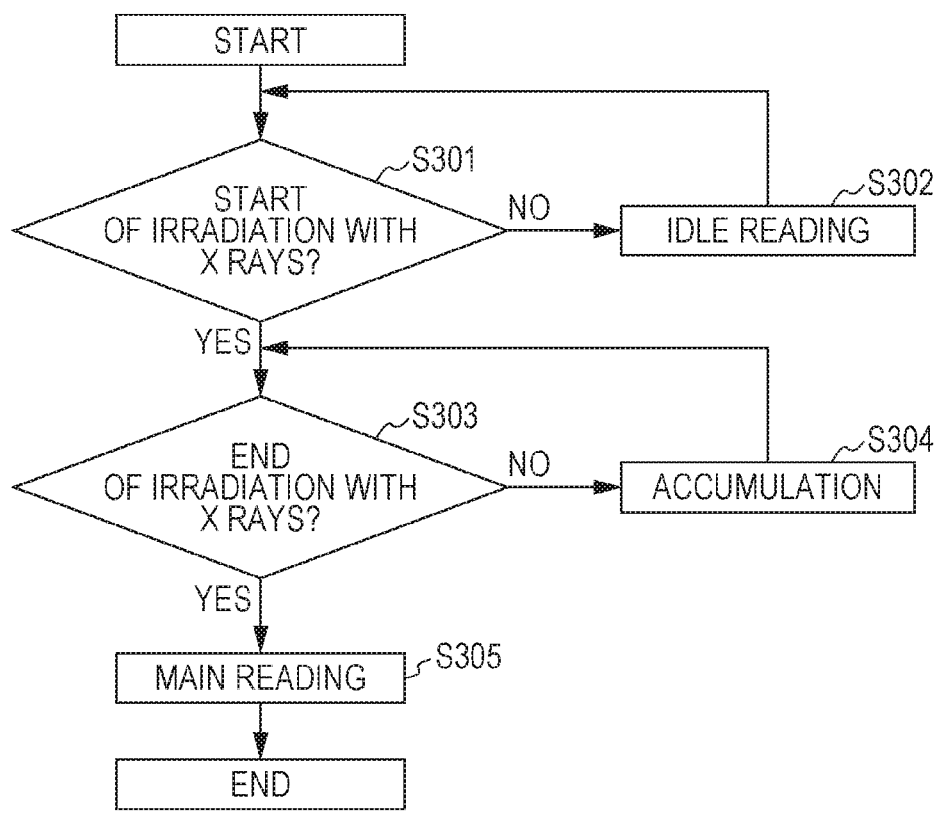
FIG. 3 is a flowchart illustrating operation of the imaging system.
Figure 4:
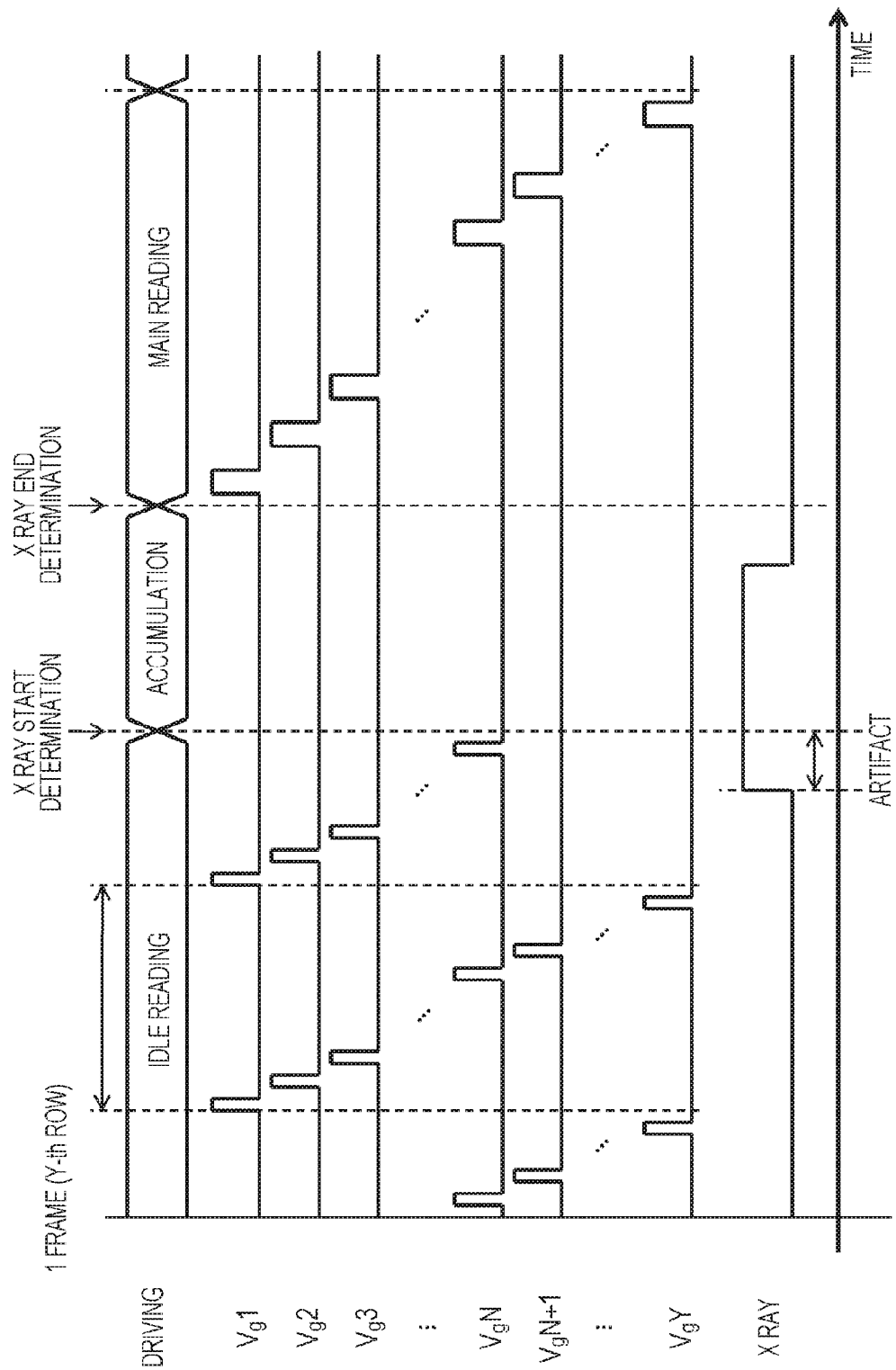
FIG. 4 is a timing chart of driving of the 2D detection unit.

FIG. 3 is a flowchart illustrating a method for controlling the radiation imaging system illustrated in FIG. 1, and FIG. 4 is a timing chart of the control method. In step S301, the driving control means 204 determines whether irradiation with X rays has been started. When receiving a signal indicating irradiation with X rays from the X-ray control apparatus 202, the X-ray generation apparatus 201 emits X rays. When receiving the signal indicating irradiation with X rays from the X-ray control apparatus 202, the driving control means 204 determines that irradiation with X rays has been started, and otherwise, determines that irradiation with X rays has not been started. When irradiation with X rays has been started, the process proceeds to step S303 whereas when irradiation with X rays has not been started, the process proceeds to step S302. In step S302, the detection unit 112 applies conductive voltages to driving lines Vg1 to VgY under control of the driving control means 204 as illustrated in FIG. 4 so as to successively bring the switch elements T11 to T33 and so on into conductive states for individual rows. By this, a resetting operation (hereinafter referred to as an "idle reading") of resetting charges in the conversion elements S11 to S33 and so on generated by charge accumulation of dark current is successively performed on the first row to a Y-th row, that is, a leading row to a last row. Thereafter, the process returns to step S301. The detection unit 112 repeatedly performs the resetting operation of resetting the charges of the conversion elements S11 to S33 and so on generated due to the dark current before the irradiation with X rays. The idle reading is successively performed from the first row to the Y-th row, that is, the leading row to the last row. When the last Y-th row is reached, the leading first row is processed again, and the idle reading is repeatedly performed in this way until start of X rays is determined. When irradiation with X rays is determined, the idle reading is stopped. The idle reading is stopped in an N-th row, for example.

In step S303, the driving control means 204 determines whether the irradiation with X rays has been terminated. For example, the driving control means 204 determines end of the irradiation with X rays when a predetermined period of time (an X-ray irradiation period) is elapsed after a time when the start of the irradiation with X rays is determined. Furthermore, the driving control means 204 may determine that the irradiation with X rays has been terminated when supply of the signal indicating irradiation with X rays from the X-ray control apparatus 202 is stopped. When the irradiation with X rays is terminated, the process proceeds to step S305, and otherwise, the process proceeds to step S304. In step S304, the detection unit 112 performs an operation of accumulating charges under control of the driving control means 204. Thereafter, the process returns to step S303. In the operation of accumulating charges, nonconductive voltages are applied to all the driving lines Vg1 to VgY so that the switch elements T11 to T33 and so on of all the pixels are brought into nonconductive states and charges corresponding to the irradiation with X rays are accumulated in the conversion elements S11 to S33 and so on. The operation of accumulating charges is performed on the conversion elements S11 to S33 and so on until the irradiation with X rays is terminated.

In step S305, the detection unit 112 performs a main reading operation of reading pixel values of the charges of the pixels corresponding to the irradiation with X rays under control of the driving control means 204. In the main reading operation, pulses of conductive voltages are successively applied to the driving lines Vg1 to VgY, the switch elements S11 to S33 and so on are successively brought into conductive states for each row, and electric signals are successively output to the signal lines Sig1 to Sig3 and so on for each row from the pixels in the leading row to the pixels in the last row. The A/D converter 110 outputs image information on the pixels in a range from the leading row to the last row to the computer 206.

Ideally, it is preferably that, before the X-ray generation apparatus 201 actually emits X rays, the driving control means 204 completes the X-ray starting determination using the signal indicating irradiation with X rays output from the X-ray control apparatus 202, and the idle reading is shifted to the charge accumulation operation. However, depending on a communication speed between the apparatuses and a period of time required for the X-ray starting determination, irradiation with X rays may be started before the idle reading is shifted to the charge accumulation operation. In this case, there arises a problem in that artifact is generated in an image which has been subjected to the idle reading after irradiation with X rays is started. Specifically, in the conversion elements S11 to S33 and so on in the vicinity of the N-th row where the idle reading is stopped, charges generated so as to correspond to the irradiation with X rays are reset by the idle reading, and accordingly, artifact corresponding to the charges which are lost due to the resetting is generated.

Figure 5:
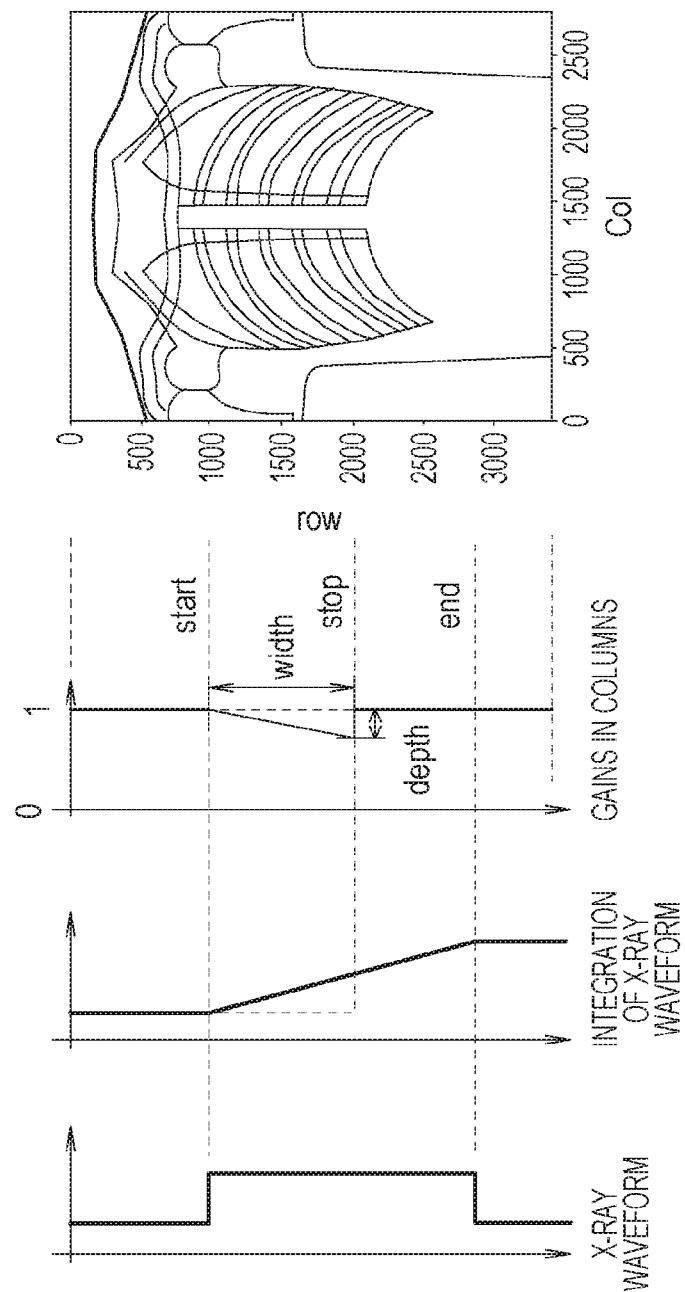
FIG. 5 is a diagram illustrating artifact in the 2D detection unit.

FIG. 5 is a diagram illustrating the artifact generated when the irradiation with X rays is started before the idle reading operation is shifted to the charge accumulation operation. If the idle reading operation is performed on a certain row in a period of time from a start time when the irradiation with X rays is actually started to a stop time when the idle reading operation is stopped, charges accumulated in this period of time in the certain row are lost. Here, amounts of lost charges are proportional to pixel values. Specifically, artifact is generated owing to reduction of gains of the pixel values. Furthermore, the charges lost in this case are proportional to an integration value of an X-ray waveform. Specifically, an amount of the artifact and the integration value of the X-ray waveform have correlation.

For simplicity of description, in a case where an X ray is approximated to a rectangular wave, an integration value of a waveform of the X ray corresponds to a straight line having a certain inclination. Accordingly, gains of pixel values in the individual rows are linearly reduced. The reduction of the gains may be represented by a depth and a width of the artifact. Note that, a case where an X ray is not a rectangular wave will be described with reference to FIG. 12. A method for calculating the width of the artifact will also be described with reference to FIG. 12. In a description below, it is assumed that an X ray may be approximated to a rectangular wave and the width of the artifact is obtained in advance.

Next, portions before and after the row where the idle reading is stopped are focused. Since a pixel before the idle reading is stopped has been subjected to the idle reading after the irradiation with X rays is started, a charge in the pixel is lost due to the idle reading. On the other hand, since a pixel after the idle reading is stopped has not been subjected to the idle reading after the irradiation with X rays is started, a charge in the pixel is not lost. Here, it is expected that values of pixels positioned close to each other are substantially the same in a most region in an image. Specifically, pixel values in a row before the idle reading is stopped and pixel values in a row after the idle reading is stopped are substantially the same if charges are not lost owing to the idle reading. By utilizing the relationship between the pixel values in the row before the idle reading is stopped and the pixel values in the row after the idle reading is stopped, amounts of reduction of gains, that is, a depth of the artifact, may be calculated. A method for calculating the depth will be described hereinafter with reference to FIGS. 6 and 7.

Note that values of pixels positioned close to each other are not substantially the same in a region in which sharp edges of a subject overlap with each other in the image. This problem will be described with reference to FIG. 13. A description below is made while it is assumed that values of pixels positioned close to each other are substantially the same.

If the depth and the width of the artifact are obtained in advance, amounts of reduction of gains of the pixel values in the individual rows may be estimated. That is, the reduction of the gains in the image may be corrected. Note that offset components are added to the pixel values owing to dark current in the image in practice. To remove the offset components, a dark image obtained by performing the main reading before or after an X-ray image is obtained is preferably subtracted from the X-ray image obtained by performing the main reading after the irradiation with X rays. However, the offset components may remain owing to a time response of the dark current even when the dark image is subtracted. The inventor found a problem in that the artifact remains if only amounts of reduction of gains are corrected while the offset components are ignored. Specifically, the correction is required to be performed after an offset correction coefficient and a gain correction coefficient are calculated in order to enhance accuracy of the correction.

Therefore, the correction coefficient obtaining means 207 sets a pair of a first pixel value of a pixel which is included in a row which has been subjected to the idle reading after the irradiation with X rays is started and a second pixel value of a pixel which is included in a row which has not been subjected to the idle reading after the irradiation with X rays is started and which is included in a column including the pixel having the first pixel value. Then the correction coefficient obtaining means 207 calculates an offset correction coefficient and a gain correction coefficient for the artifact generated in the image using a plurality of such pairs of values which belong to different columns. The image correction means 208 corrects the artifact generated in the image using the offset correction coefficient and the gain correction coefficient.

Figure 6:
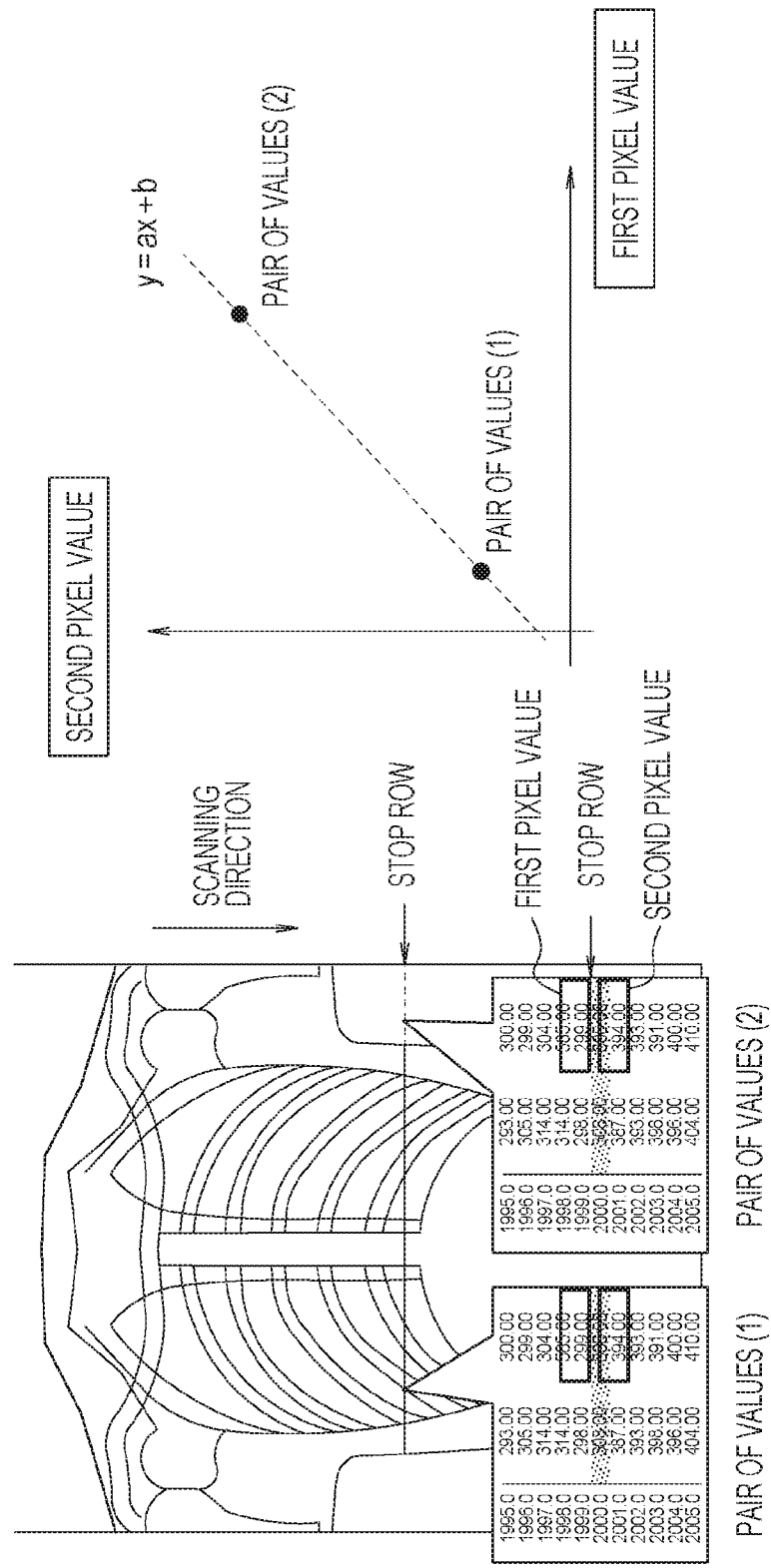
FIG. 6 is a diagram illustrating a method for calculating correction coefficients employed in correction coefficient obtaining means.

FIG. 6 is a diagram illustrating a method for calculating correction coefficients employed in the correction coefficient obtaining means 207. First, using two pairs of values described above, an inclination a and an intercept b of a straight line which connects the pairs of values to each other are obtained. The offset correction coefficient and the gain correction coefficient may be calculated using the inclination a and the intercept b. A method for the calculation will be described in detail with reference to FIG. 7.

When the inclination a and the intercept b of the straight line which connects the pairs of values to each other are to be obtained, at least two valid pairs of values are required. However, values of a pair which are extracted from different rows in the same column are substantially the same as each other since pixels thereof are positioned close to each other. In this case, there arises a problem in that calculation accuracy of the inclination a and the intercept b is considerably degraded. Accordingly, a plurality of pairs of values which are included in different columns are preferably used.

Furthermore, to satisfy an assumption that values of pixels positioned close to each other are substantially the same, a row of the first pixel value and a row of the second pixel value are preferably positioned close to each other. In particular, it is preferable that a boundary portion between a row which has been subjected to the idle reading after the X-ray irradiation is started and a row which has not been subjected to the idle reading after the X-ray irradiation is started, that is, a pixel value in the N-th row where the idle reading is stopped and a pixel value in a next row, that is, an (N+1)-th row, are preferably used. In this case, the first pixel value belongs to the N-th row where the idle reading is stopped and the second pixel value belongs to the (N+1)-th row immediately after the N-th row where the idle reading is stopped.

However, when the idle reading is stopped, an error may occur in the pixel values in the N-th row where the idle reading is stopped. In this case, it is preferable that pixel values in a row before the N-th row where the idle reading is stopped and the row after the N-th row where the idle reading is stopped in a scanning direction are used. In this case, the first pixel value is a pixel value of a pixel which belongs to an (N−1)-th row immediately before the N-th row where the idle reading is stopped and the second pixel value is a pixel value of a pixel which belongs to the (N+1)-th row immediately after the N-th row where the idle reading is stopped.

Furthermore, in general, it is likely that accuracy of the correction coefficients is improved as the number of pairs of values is larger. If a large number of pairs of values may be obtained, the inclination a and the intercept b are preferably obtained by a least-square method. In this case, the pairs of values may be obtained from all or some of columns in the rows before and after the row where the idle reading is stopped.

Furthermore, the correction coefficient obtaining means 207 preferably uses a row number of the row where the idle reading is stopped, as the idle reading stop row N, which is output from the driving control means 204. Moreover, the correction coefficient obtaining means 207 may calculate a row number where the idle reading is stopped in accordance with image information in a case where implement of a protocol for transferring a value of such a row number is difficult.

Figure 7:
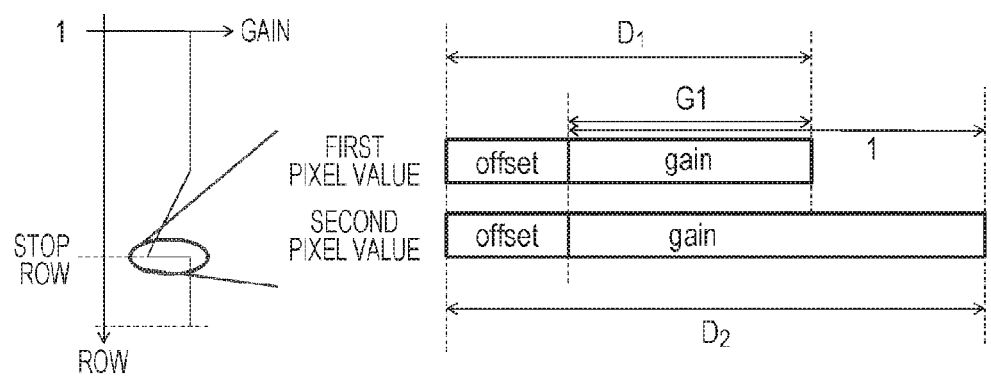
FIG. 7 is a diagram illustrating a method for calculating an offset correction coefficient and a gain correction coefficient.

FIG. 7 is a diagram illustrating a method for obtaining an offset correction coefficient and a gain correction coefficient in accordance with the inclination a and the intercept b of the straight line which connects the plurality of pairs of values to each other. As illustrated in FIG. 7, a pixel value is constituted by an offset component "offset" generated by dark current or the like and a gain component "gain" generated by an X ray. In the vicinity of the idle reading stop row N, offset components "offset" of a first pixel value D1 and a second pixel value D2 are substantially the same as each other. Furthermore, since the first pixel value D1 has been subjected to the idle reading, a gain component "gain" of the first pixel value D1 is reduced to G1 times a gain component "gain" of the second pixel value D2. Since the first pixel value D1 and the first pixel value D2 are positioned close to each other, the first pixel value D1 and the second pixel value D2 are substantially the same as each other if the idle reading is not performed on the first pixel value D1. Accordingly, the relationship between the first pixel value D1 and the second pixel value D2 is represented by Expression (1) below.

$$\{D2-\text{offset}\}:1=\{D1-\text{offset}\}:G1 \quad \text{Expression (1)}$$

Furthermore, as illustrated in FIG. 6, the relationship between the first pixel value D1 and the second pixel value D2 is represented by Expression (2) below.

$$D2=a\times D1+b \quad \text{Expression (2)}$$

Accordingly, the offset correction coefficient "offset" indicating an offset component and the gain correction coefficient G1 are represented by Expression (3) below.

$$\text{offset}=b/(1-a) \quad G1=1/a \quad \text{Expression (3)}$$

Figure 8:
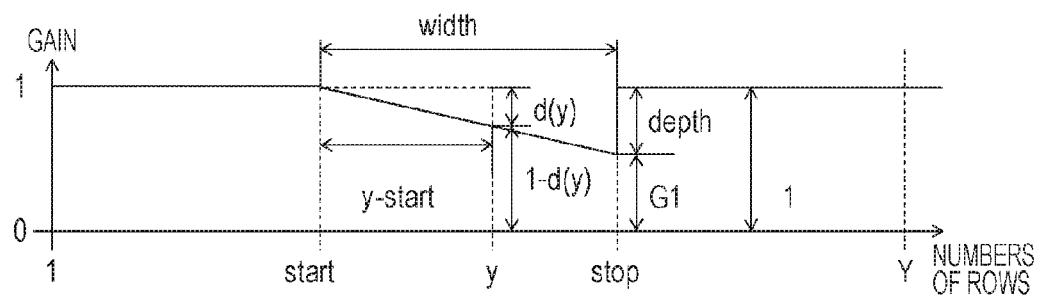
FIG. 8 is a diagram illustrating a method for correcting an image employed in image correction means.

FIG. 8 is a diagram illustrating a method for correcting pixel values in an interval in which the idle reading is performed after X rays are actually emitted. First, a row where irradiation with X rays is actually started is denoted by "start" and a row where the irradiation with X rays is stopped is denoted by "stop". The width of a step is obtained in advance as described with reference to FIG. 5. The relationship among "start", "stop", and "width" is represented by Expression (4).

$$\text{start}=\text{stop}-\text{width} \quad \text{Expression (4)}$$

Furthermore, a depth of artifact in a boundary between the first and second pixel values is represented by Expression (5) below.

$$\text{depth}=1-G1 \quad \text{Expression (5)}$$

As illustrated in FIG. 8, an artifact amount d(y) in an interval of a row which has been subjected to the idle reading after the irradiation with X rays is actually started, that is, a y-th row (start<y<stop), is represented by Expression (6) below.

$$\text{width}:\text{depth}=\{y-\text{start}\}:d(y) \quad \text{Expression (6)}$$

According to Expression (4) to Expression (6), Expression (7) below is obtained.

$$d(y)=(1-G1)\times(y-\text{stop}+\text{width})/\text{width} \quad \text{Expression (7)}$$

Although an offset component of a pixel value in the y-th row is not reduced, a gain component is reduced to 1-d(y) times a gain component to be obtained. Accordingly, assuming that a pixel value in an x-th column and a y-th row is denoted by D(x, y) and a value of a pixel where the artifact is corrected is denoted by D'(x, y), Expression (8) below is obtained.

$$\{D'(x,y)-\text{offset}\}\times\{1-d(y)\}=D(x,y)-\text{offset} \quad \text{Expression (8)}$$

The artifact is not generated in an interval in a row which has not been subjected to the idle reading after the irradiation with X rays is actually started. Accordingly, assuming that the number of rows in the 2D detection unit 205 is Y, an image D'(x, y) which has been corrected is represented by Expression (9) below.

$$D'(x,y)=D(x,y)$$

$$(0\leq y\leq \text{start})$$

$$D'(x,y)=D(x,y)+\{D(x,y)-\text{offset}\}\times d(y)/\{1-d(y)\}$$

$$(\text{start}<y<\text{stop}) \quad D'(x,y)=D(x,y)$$

$$(\text{stop}\leq y\leq Y-1) \quad \text{Expression (9)}$$

In this way, an image having the pixel values in the interval of the row which has been subjected to the idle reading after the irradiation with X rays is actually started which are reliably corrected may be obtained. Note that, in a case where the idle reading returns to the leading row in the period of time from when the irradiation with X rays is actually started to when the idle reading is stopped, image correction is performed in accordance with Expression (10) below.

$$D'(x,y)=D(x,y)+\{D(x,y)-\text{offset}\}\times d(y)/\{1-d(y)\}$$

$$(0 \leq y < \text{stop})$$

$$D'(x,y)=D(x,y)$$

$$(\text{stop} \leq y \leq \text{start})$$

$$D'(x,y)=D(x,y)+\{D(x,y)-\text{offset}\}\times d(y-Y)/\{1-d(y-Y)\}$$

$$(\text{stop} < y \leq Y-1) \quad \text{Expression (10)}$$

According to the correction method described above, if start of irradiation with X rays may be determined before the idle reading makes a round after the irradiation with X rays is started, an image is obtained while artifact generated before the determination is corrected. That is, a time limit by the time when start of the irradiation with X rays is determined may be considerably mitigated.

(Second Embodiment)

Figure 9:
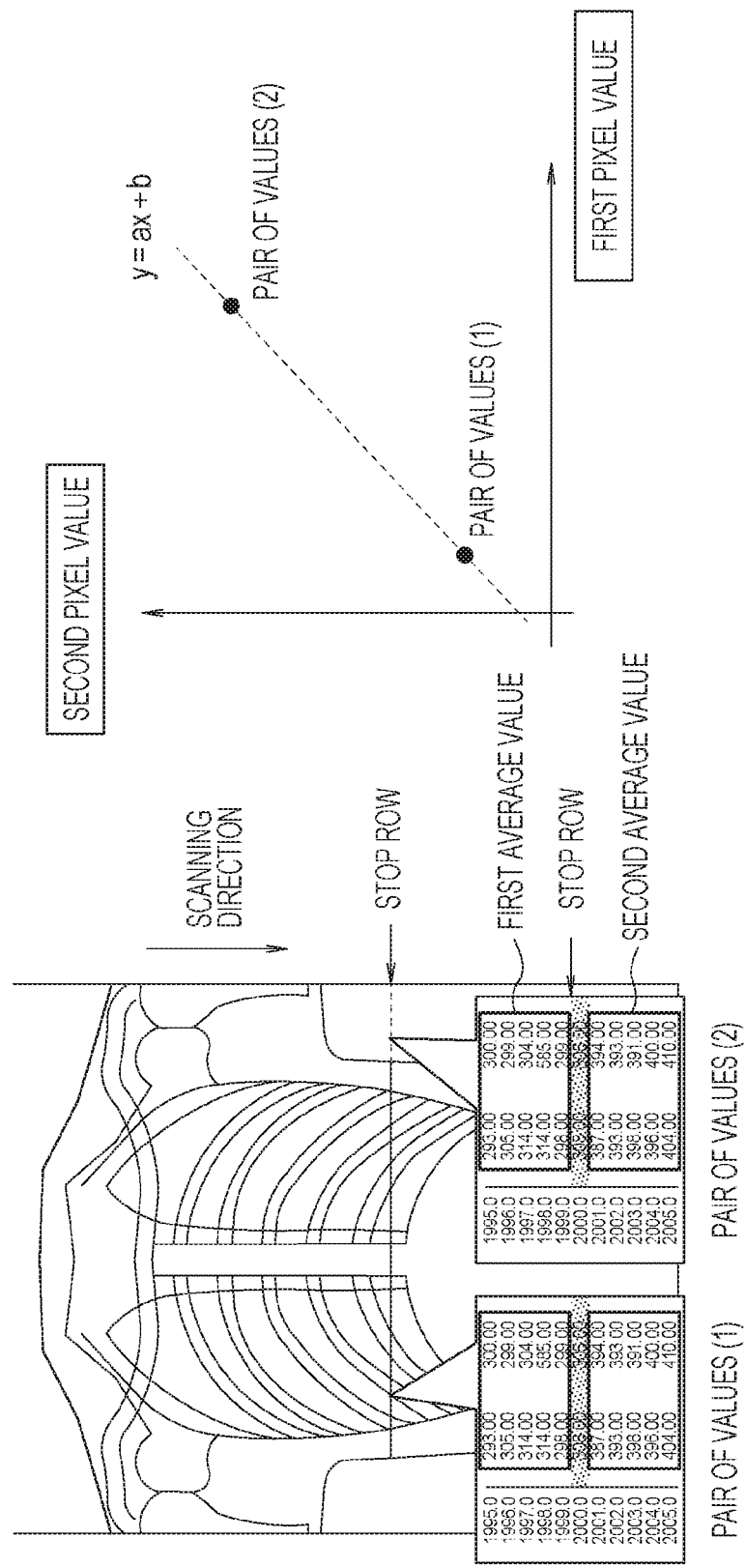
FIG. 9 is a diagram illustrating a method for calculating correction coefficients according to a second embodiment.

A second embodiment of the present invention is the same as the first embodiment except for a method for obtaining an inclination a and an intercept b of a straight line illustrated in FIG. 6. FIG. 9 corresponds to FIG. 6 and is a diagram illustrating the method for obtaining an inclination a and an intercept b of a straight line according to the second embodiment of the present invention. Hereinafter, portions different from the first embodiment in this embodiment will be described. Correction coefficient obtaining means 207 obtains pixel values of a plurality of pixels included in a row which has been subjected to idle reading after irradiation with X rays is started and averages the pixel values so as to obtain a first average value in a certain region of interest. Thereafter, the correction coefficient obtaining means 207 obtains pixel values of a plurality of pixels which are included in a row which has not been subjected to the idle reading after the irradiation with X rays is started and which are included in a range of a column of the region of interest of the first average value, averages the pixel values so as to obtain a second average value in the region of interest, and sets a pair of the first and second average values. Then the correction coefficient obtaining means 207 calculates an offset correction coefficient and a gain correction coefficient for artifact generated in an image using a plurality of pairs of values which belong to different column ranges. Since noise included in the pixel values is averaged in this embodiment, pairs of values may be obtained with higher accuracy when compared with the first embodiment. Accordingly, this embodiment is advantageous in that accuracy of the offset correction coefficient and the gain correction coefficient is improved.

As with the first embodiment, values which are paired and obtained in the same column range are substantially the same value in this embodiment since pixels of the values are positioned close to each other. Specifically, there arises a problem in that calculation accuracy of an inclination a and an intercept b is considerably degraded. Therefore, at least two pairs of values which belong to column ranges which do not overlap with each other are required. However, in a case where an entire row in the image is specified as the region of interest, only a single column range is obtained, and accordingly, only one valid pair of values may be obtained. Therefore, there arises a problem in that, even if row average of the image, that is, profile analysis, is performed, an offset correction coefficient and a gain correction coefficient may not be calculated. Consequently, a configuration in which the offset correction coefficient and the gain correction coefficient are calculated using the profile analysis of the image is excepted in this embodiment.

(Third Embodiment)

Figure 10:
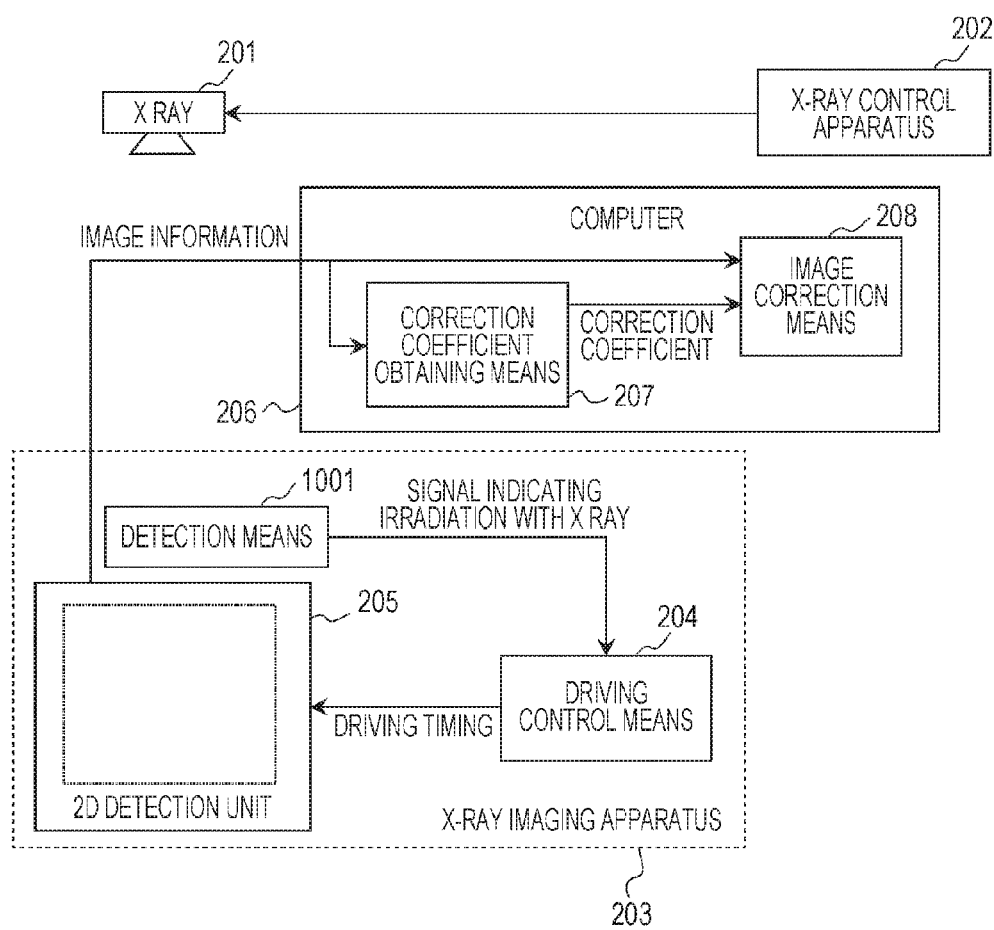
FIG. 10 is a block diagram illustrating an imaging system according to a third embodiment.

FIG. 10 is a block diagram illustrating a configuration of a radiation imaging system according to a third embodiment of the present invention. In FIG. 10, detection means 1001 is added to the configuration illustrated in FIG. 1. Hereinafter, portions different from the first embodiment in this embodiment will be described. The detection means 1001 detects start and end of irradiation with X rays and outputs a signal indicating the irradiation with X rays to driving control means 204. The driving control means 204 receives the signal indicating the irradiation with X rays from the detection means 1001 and controls operation of a 2D detection unit 205 instead of an X-ray control apparatus 202. By this, an X-ray imaging apparatus 203 may perform imaging without being connected to the X-ray control apparatus 202.

Figure 11:
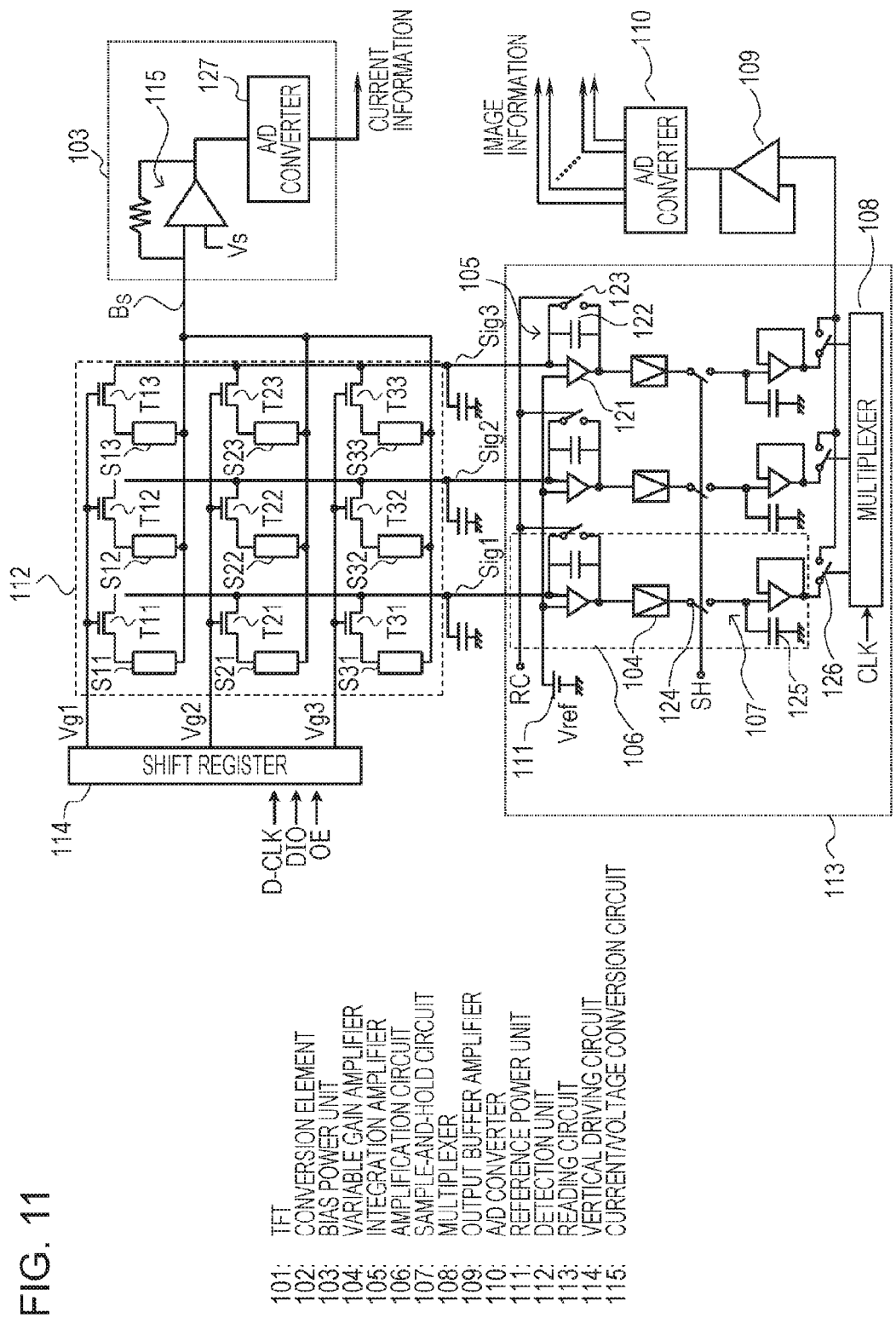
FIG. 11 is a diagram illustrating an equivalent circuit of a 2D detection unit.

FIG. 11 is a diagram illustrating a configuration of the 2D detection unit 205 of FIG. 10. FIG. 11 is different from FIG. 2 in a configuration of a bias power unit 103. The bias power unit 103 includes a current/voltage conversion circuit 115 and an A/D converter 127. The current/voltage conversion circuit 115 converts current supplied to a bias line Bs into voltage while supplying a bias voltage Vs to the bias line Bs and outputs the voltage to the A/D converter 127. The A/D converter 127 converts an analog voltage value including current information into a digital voltage value including the current information to be output. The detection means 1001 of FIG. 10 detects start and end of the irradiation with X rays using the current information output from the A/D converter 127. By this, the detection means 1001 which detects the irradiation with X rays may be implemented without installation of an X-ray sensor other than the 2D detection unit 205.

Figure 12:
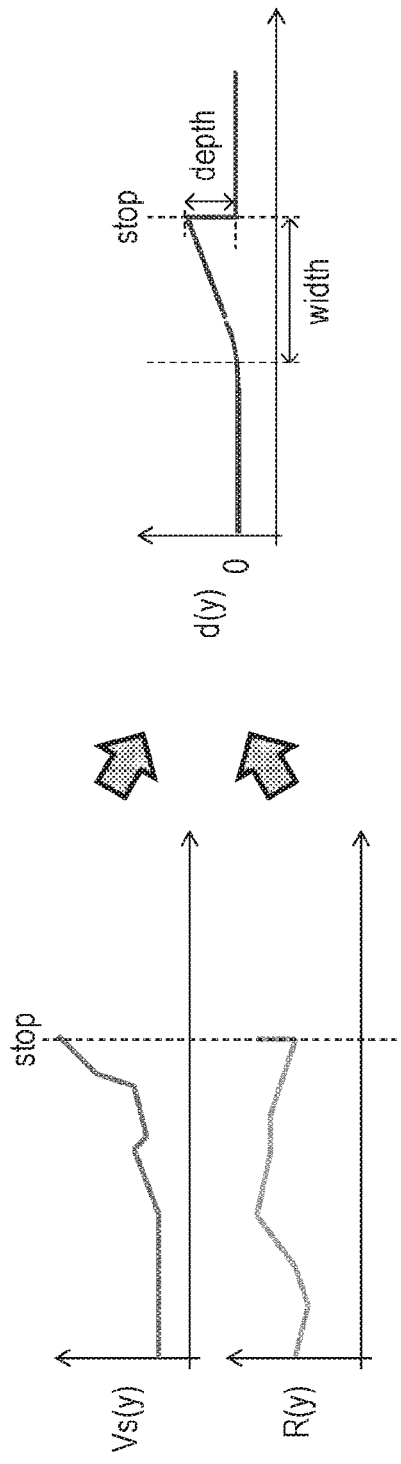
FIG. 12 is a diagram illustrating a method for estimating a shape and a width of artifact.

FIG. 12 is a diagram illustrating a method for estimating a shape and a width of artifact according to this embodiment. In the description above, it is assumed that a waveform of an X ray is rectangle and a width of artifact is obtained in advance as described with reference to FIG. 5. However, the width of the artifact considerably varies in practice depending on a period of time of irradiation with X rays. Therefore, a correction error may be generated unless the width of the artifact is reliably estimated. As a method for estimating the width, analysis of a profile of an image may be employed. However, since the image includes information on a subject, the estimation of the width is difficult. Furthermore, it is not necessarily the case that the waveform of an X ray is rectangle. In particular, in a case where the period of time of irradiation with X rays is short, influence of rising and falling of the waveform of the X ray is not negligible.

Accordingly, the inventor proposes a method using a signal indicating irradiation with X rays in addition to image information. Use of this method may improve accuracy of estimation of a width of artifact, and in addition, estimate a shape of the artifact generated by an arbitrary X-ray waveform. By an experiment, the inventor found that an amount of signal charge lost from the image and a value of a current supplied to the bias line Bs are proportional to each other.

First, as with the description with reference to FIG. 8, it is assumed that an image before correction is denoted by D(x, y), a number of a row where idle reading is stopped is denoted by "stop", an offset correction coefficient is denoted by "offset", and a depth of the artifact is denoted by "depth". Furthermore, it is assumed that the number of columns in a 2D detection unit 205 is denoted by "X". Here, a sum R(y) of gain components of pixel values in a y-th row is represented by Expression (11) below.

$$R(y)=\{D(0,y)\text{-offset}\}+\{D(1,y)\text{-offset}\}+\ldots+\{D(X-1,y)\text{-offset}\}=\Sigma D(x,y)\text{-offset}\times X \quad \text{Expression (11)}$$

The inventor straightens the relationship among the sum R(y) of the gain components of the pixel values in the y-th row, a current Vs(y) supplied to the bias line Bs when the idle reading is performed on the y-th row, and an artifact amount d(y) in the y-th row. As a result, the inventor found that Expression (12) below is satisfied not only in a case where X rays having a waveform of a rectangular shape are emitted but also in a case where X rays having an arbitrary waveform are emitted. Here, "α" denotes a proportional constant.

$$R(y)\times d(y)/\{1-d(y)\}=\alpha\times Vs(y) \quad \text{Expression (12)}$$

An artifact amount in a case where "y=stop" is satisfied corresponds to an artifact depth. When "y=stop" is assigned to Expression (12), Expression (13) below is obtained.

$$R(\text{stop})\times d(\text{stop})/\{1-d(\text{stop})\}=\alpha\times Vs(\text{stop}) \quad \text{Expression (13)}$$

When Expression (12) and Expression (13) are arranged and the proportion coefficient α is removed, Expression (14) is obtained.

$$\{1-d(y)\}/d(y)=(1-\text{depth})/\text{depth}\times Vs(\text{stop})/Vs(y)\times R(y)/R(\text{stop}) \quad \text{Expression (14)}$$

According to Expression (14), the artifact amount d(y) in the y-th row may be obtained as represented by Expression (15) below.

$$d(y)=1/[\{Vs(\text{stop})\times R(y)\times(1-\text{depth})\}/\{R(\text{stop})\times Vs(y)\times\text{depth}\}+1] \quad \text{Expression (15)}$$

In this way, amounts d(y) of artifact in individual rows generated in the image, that is, shape correction coefficient strings d(y) indicating a shape of the artifact, may be obtained in the case of the arbitrary X-ray waveform. In a case where the X-ray waveform may be approximated to a rectangular wave, a width correction coefficient "width" indicating the width of the artifact generated in the image may be obtained in accordance with the shape correction coefficient strings d(y). For example, a method using a row which satisfies "d(y)=0" as a start row is preferably employed.

In the foregoing description, the shape correction coefficient strings d(y) and the width correction coefficient "width" are obtained using the current Vs(y) supplied to the bias line Bs for the pixels in addition to the image information. However, this embodiment is not limited to this. The shape correction coefficient strings d(y) and the width correction coefficient "width" may be obtained by employing a configuration in which signals indicating irradiation with X rays are extracted from some of the pixels included in the 2D detection unit 205 and by using the signals output from some of the pixels included in the 2D detection unit 205 in addition to the image information. Furthermore, the shape correction coefficient strings d(y) and the width correction coefficient "width" may be obtained by employing a configuration in which a signal indicating irradiation with X rays is extracted from an X-ray sensor disposed independently from the 2D detection unit 205 and by using the signal output from the X-ray sensor in addition to the image information.

FIG. 13(A) to FIG. 13(C) are diagrams illustrating a method for removing an abnormal pixel value. As described with reference to FIG. 5, it is assumed that values of pixels positioned close to each other are substantially the same in a most region in an image. However, this assumption is not satisfied in practice in some cases. For example, in a region in which sharp edges of a subject overlap with each other in the image, values of pixels positioned close to each other are not substantially the same due to influence of the edges. Accordingly, the assumption for calculation of an inclination a and an intercept b using pairs of values is not satisfied, and accuracy of estimation of the inclination a and the intercept b may be degraded.

Accordingly, the inventor proposes a method in which a determination of abnormality is performed on pairs of values, and pairs of values which are determined as abnormal are not used in calculation for correction coefficients. In this method, by removing the pairs of values in which the assumption required for the calculation of the inclination a and the intercept b is not satisfied, the correction coefficients, such as the offset correction coefficient and the gain correction coefficient, may be reliably calculated.

First, as illustrated in FIG. 13(A), the relationship between neighboring pixel values of first and second pixel values are focused. If a subject is uniform in the vicinity of the first pixel value, the first pixel value and the neighboring pixel values of the first pixel value are substantially the same. However, the pixel values have some variation.

If the first pixel value is large, variation caused by quantum noise of X rays is dominant whereas if the first pixel value is small, variation caused by system noise is dominant. The relationship between the first pixel value and the neighboring pixel values of the first pixel value may be included in an amount of the variation estimated by the quantum noise of the X rays and an amount of the variation estimated by the system noise. In this case, it is estimated that the assumption that values of pixels positioned close to each other are substantially the same is satisfied in the vicinity of the first pixel value. On the other hand, the relationship between the first pixel value and the neighboring pixel values of the first pixel value may be out of the amount of the variation estimated by the quantum noise of the X rays and the amount of the variation estimated by the system noise. In this case, it is estimated that the assumption that values of pixels positioned close to each other are substantially the same is not satisfied in the vicinity of the first pixel value. The same is true of the relationship between the second pixel value and neighboring pixel values of the second pixel value.

If such an abnormal pair of values is mixed, the accuracy of the estimation of the inclination a and the intercept b is degraded. Therefore, correction coefficient obtaining means 207 determines that a pair of values is abnormal if at least one of the pixel values in the pair of values is out of the variation amount estimated by the quantum noise of X rays and the system noise relative to the neighboring pixel values in FIG. 13(B). Then the correction coefficient obtaining means 207 removes the abnormal pair of values as illustrated in FIG. 13(B) before calculating the correction coefficients. The abnormal pair of values is not used for the calculation of the correction coefficients.

In the foregoing description, the correction coefficient obtaining means 207 determines that a pair of values is abnormal if at least one of the pixel values in the pair of values is out of the variation amount estimated by the quantum noise of X rays and/or the system noise relative to neighboring pixel values. However, this embodiment is not limited to this. The correction coefficient obtaining means 207 may determine that a pair of values is abnormal in a case where at least one of the pixel values in the pair of values is saturated. Furthermore, the correction coefficient obtaining means 207 may determine that a pair of values is abnormal in a case where at least one of the pixel values in the pair of values is a negative value or corresponds to a defective pixel.

Note that the foregoing embodiments may be realized when a computer included in the driving control means 204 illustrated in FIG. 1 executes a program, for example. Furthermore, means for supplying the program to the computer, such as a computer readable recording medium including a CD-ROM recording the program or a transmission medium including the Internet for transmitting the program, may be employed as an embodiment of the present invention. Furthermore, the program may be employed as an embodiment of the present invention. The program, the recording medium, the transmission medium, and a program product are included in the scope of the present invention. Moreover, inventions obtained by combinations of the first to third embodiments which are easily imagined are also included in the scope of the present invention.

The foregoing embodiments are merely exemplary embodiments of the present invention, and therefore, the technical scope of the present invention is not limited by the foregoing embodiments. That is, the present invention may be embodied by various forms without departing from the scope of the present invention or main features of the present invention.

This application claims the benefit of Japanese Patent Application No. 2013-143832 filed Jul. 9, 2013, which is hereby incorporated by reference herein in its entirety.

REFERENCE SIGNS LIST

204 DRIVING CONTROL MEANS
205 2D DETECTION UNIT
207 CORRECTION COEFFICIENT OBTAINING MEANS
208 IMAGE CORRECTION MEANS

The invention claimed is:

1. A radiation imaging system comprising:
a detection unit configured to include a plurality of pixels which are arranged in a matrix and which output pixel values by converting radial rays into charges and to output image information;
driving control means for causing the plurality of pixels to perform a resetting operation until a signal indicating irradiation with radial rays is supplied and to stop the resetting operation and perform an operation of accumulating charges when the signal indicating irradiation with radial rays is supplied, and for performing an operation of reading pixel values of the plurality of pixels after the irradiation with radial rays is terminated so as to output image information corresponding to the irradiation with radial rays;
correction coefficient obtaining means for calculating correction coefficients in accordance with the image information output from the detection unit; and
image correction means for correcting the image information output from the detection unit using the correction coefficients calculated by the correction coefficient obtaining means,
wherein the correction coefficient obtaining means sets a pair of a first pixel value of a pixel included in a row which has been subjected to the resetting operation after the irradiation with radial rays is started and a second pixel value of a pixel which is included in a row which has not been subjected to the resetting operation after the irradiation with radial rays is started and which is included in a column including the pixel having the first pixel value, and
the correction coefficients are calculated using the pair of values which belong to different columns.

2. The radiation imaging system according to claim 1, wherein the driving control means controls operation of the detection unit using a signal indicating irradiation with radial rays output from a radiation control apparatus which controls irradiation with radial rays.

3. The radiation imaging system according to claim 1, further comprising:
detection means for detecting irradiation with radial rays and outputting a signal indicating the irradiation with radial rays,
wherein the driving control means controls operation of the detection unit using the signal indicating irradiation with radial rays output from the detection means.

4. The radiation imaging system according to claim 1, wherein
the correction coefficient obtaining means sets a pair of a first average value obtained by averaging pixel values of a plurality of pixels included in a row which has been subjected to the resetting operation after the irradiation with radial rays is started and a second average value obtained by averaging pixel values of a plurality of pixels which are included in a row which has not been subjected to the resetting operation after the irradiation with radial rays is started and which are included in columns including the plurality of pixels used for generating the first average value, and
the correction coefficients are calculated using a plurality of pairs of values included in different columns.

5. The radiation imaging system according to claim 1, wherein the correction coefficient obtaining means calculates the correction coefficients using a least-square method.

6. The radiation imaging system according to claim 1, wherein the correction coefficient obtaining means calculates the correction coefficients in accordance with a row number of a row where the resetting operation is stopped.

7. The radiation imaging system according to claim 6, wherein the correction coefficient obtaining means calculates the correction coefficients in accordance with the row number of the row where the resetting operation is stopped which is input by the driving control means.

8. The radiation imaging system according to claim 6, wherein the correction coefficient obtaining means calculates the correction coefficient in accordance with the row number of the row where the resetting operation is stopped which is calculated in accordance with the image information.

9. The radiation imaging system according to claim 6, wherein the first pixel value is a pixel value of a pixel included in the row where the resetting operation is stopped, and the second pixel value is a pixel value of a pixel included in a row immediately after the row where the resetting operation is stopped.

10. The radiation imaging system according to claim 6, wherein the first pixel value is a pixel value of a pixel included in a row immediately before the row where the resetting operation is stopped, and the second pixel value is a pixel value of a pixel included in a row immediately after the row where the resetting operation is stopped.

11. The radiation imaging system according to claim 1, wherein the correction coefficients include an offset correction coefficient, a gain correction coefficient, and a width correction coefficient indicating a width of artifact generated in an image.

12. The radiation imaging system according to according to claim 1, wherein the correction coefficients include an offset correction coefficient, a gain correction coefficient, and shape correction coefficient strings indicating amounts of artifact in individual rows generated in an image.

13. The radiation imaging system according to claim 11, wherein the correction coefficient obtaining means calculates the width correction coefficient or the shape correction coefficient strings in accordance with the image information.

14. The radiation imaging system according to claim 11, wherein the correction coefficient obtaining means calculates the width correction coefficient or the shape correction coefficient strings in accordance with current supplied to a bias line of the pixels.

15. The radiation imaging system according to claim 1, wherein the correction coefficient obtaining means removes, when the pair of values is abnormal, the abnormal pair of values before calculating the correction coefficients.

16. The radiation imaging system according to claim 15, wherein the correction coefficient obtaining means determines that the pair of values is abnormal in a case where at least one of the pixel values in the pair of values is out of an amount of variation estimated from quantum noise relative to neighboring pixel values.

17. The radiation imaging system according to claim 15, wherein the correction coefficient obtaining means determines that the pair of values is abnormal in a case where at least one of the pixel values in the pair of values is out of an amount of variation estimated from system noise relative to neighboring pixel values.

18. The radiation imaging system according to claim 15, wherein the correction coefficient obtaining means determines that the pair of values is abnormal in a case where at least one of the pixel values in the pair of values is saturated.

19. The radiation imaging system according to claim 15, wherein the correction coefficient obtaining means determines that the pair of values is abnormal in a case where at least one of the pixel values in the pair of values is a negative value.

20. The radiation imaging system according to claim 15, wherein the correction coefficient obtaining means determines that the pair of values is abnormal in a case where at least one of the pixel values in the pair of values corresponds to a defective pixel.

* * * * *